(12) United States Patent
Morgan et al.

(10) Patent No.: US 8,900,133 B2
(45) Date of Patent: Dec. 2, 2014

(54) CAPSULE IMAGING DEVICES, SYSTEMS AND METHODS FOR IN VIVO IMAGING APPLICATIONS

(75) Inventors: Douglas R. Morgan, Chapel Hill, NC (US); P. Kay Lund, Carrboro, NC (US); Howard H. Zhang, Hudson, OH (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1173 days.

(21) Appl. No.: 11/920,314

(22) PCT Filed: May 12, 2006

(86) PCT No.: PCT/US2006/018513
§ 371 (c)(1),
(2), (4) Date: Mar. 6, 2009

(87) PCT Pub. No.: WO2006/124648
PCT Pub. Date: Nov. 23, 2006

(65) Prior Publication Data
US 2009/0216079 A1    Aug. 27, 2009

Related U.S. Application Data

(60) Provisional application No. 60/680,580, filed on May 13, 2005, provisional application No. 60/742,199, filed on Dec. 2, 2005.

(51) Int. Cl.
| | | |
|---|---|---|
| *A61B 1/06* | (2006.01) | |
| *A61B 1/04* | (2006.01) | |
| *A61B 5/00* | (2006.01) | |
| *A61B 1/00* | (2006.01) | |

(52) U.S. Cl.
CPC ............... *A61B 5/42* (2013.01); *A61B 1/0676* (2013.01); *A61B 1/043* (2013.01); *A61B 5/0071* (2013.01); *A61B 1/00186* (2013.01); *A61B 5/0084* (2013.01); *A61B 1/041* (2013.01); *A61B 1/0684* (2013.01); *A61B 1/0646* (2013.01)
USPC ........................... 600/160; 600/109; 600/181

(58) Field of Classification Search
USPC ............ 600/109, 160, 476, 178, 181; 424/9.6
See application file for complete search history.

(56) References Cited

U.S. PATENT DOCUMENTS

| | | |
|---|---|---|
| 5,604,531 A | 2/1997 | Iddan et al. |
| 6,363,373 B1 | 3/2002 | Steinkraus |

(Continued)

OTHER PUBLICATIONS

Communication pursuant to Article 94(3) EPC dated Nov. 30, 2009 for EPO Application No. 067 702 95.1.

(Continued)

*Primary Examiner* — Anhtuan T Nguyen
*Assistant Examiner* — William Chou
(74) *Attorney, Agent, or Firm* — Jenkins, Wilson, Taylor & Hunt, P.A.

(57) ABSTRACT

Novel capsule imaging devices, systems and methods are provided for in vivo imaging applications, such as for gastrointestinal applications. A swallowable video imaging device, such as a capsule, can be used with a light filter for in vivo illumination of a target tissue that has absorbed a previously administered biological probe. The target tissue can be distinguished in images transmitted from the video imaging device. Quantification of the signal intensity of fluorescence can be used to assess how progressed the target tissue may be. The target tissue can be therapeutically treated to shrink or kill the target tissue.

9 Claims, 11 Drawing Sheets

(56) References Cited

U.S. PATENT DOCUMENTS

| | | | |
|---|---|---|---|
| 6,529,847 | B2 | 3/2003 | Hamilton et al. |
| 6,592,847 | B1 | 7/2003 | Weissleder et al. |
| 6,632,175 | B1 | 10/2003 | Marshall |
| 6,704,043 | B2 | 3/2004 | Goldstein et al. |
| 6,807,446 | B2 | 10/2004 | Fenn et al. |
| 6,939,292 | B2 | 9/2005 | Mizuno |
| 6,986,738 | B2 | 1/2006 | Glukhovsky et al. |
| 7,009,634 | B2 | 3/2006 | Iddan et al. |
| 7,022,067 | B2 | 4/2006 | Glukhovsky et al. |
| 7,653,429 | B2 * | 1/2010 | Madar et al. .................. 600/476 |
| 2002/0026108 | A1 * | 2/2002 | Colvin, Jr. .................... 600/316 |
| 2003/0207264 | A1 * | 11/2003 | Packard et al. .................. 435/6 |
| 2003/0219383 | A1 | 11/2003 | Weissleder et al. |
| 2004/0092825 | A1 * | 5/2004 | Madar et al. .................. 600/473 |
| 2004/0176669 | A1 * | 9/2004 | Colvin, Jr. .................... 600/316 |
| 2004/0197267 | A1 * | 10/2004 | Black et al. .................... 424/9.6 |
| 2004/0210289 | A1 * | 10/2004 | Wang et al. .................. 607/116 |
| 2004/0249245 | A1 * | 12/2004 | Irion ............................ 600/160 |
| 2004/0254419 | A1 * | 12/2004 | Wang et al. ....................... 600/8 |
| 2005/0029437 | A1 | 2/2005 | Hasegawa et al. |
| 2005/0043587 | A1 | 2/2005 | Fujimori et al. |
| 2005/0154277 | A1 * | 7/2005 | Tang et al. ..................... 600/407 |
| 2005/0215911 | A1 * | 9/2005 | Alfano et al. ................. 600/476 |
| 2006/0030754 | A1 | 2/2006 | Iddan |
| 2007/0225634 | A1 * | 9/2007 | Ferren et al. .................... 604/27 |

OTHER PUBLICATIONS

*PillCam ESO Capsule Endoscopy*, Retrieved May 6, 2005, from http://www.givenimaging.com/Cultures/en-US/Given/English/Products/ESO_CE/.

Mahmood, U., & Weissleder, R., *Near-Infrared Optical Imaging of Proteases in Cancer*. Molecular Cancer Therapy vol. 2, 489-496 (2003).

Tung, C., *Fluorescent Peptide Probes for in Vivo Diagnostic Imaging*. Biopolymers (Peptide Science), vol. 76, 391-403 (2004).

Weissleder, R., & Ntziachristos, V., *Shedding Light Onto Live Molecular Targets*. Nature Medicine vol. 9, No. 1 (2003).

Carrington, C. (Nov. 2003). *Molecular Imaging Outlook, NIRF measures response to arthritis therapy*, Retrieved Jan. 18, 2008, from http://www.diagnosticimaging.com/molecularimagingoutlook/2003nov/07.jhtml.

Bankhead, C. (Nov. 2005). *Molecular Imaging Outlook, Cathepsin-sensing optical probe detects breast cancer lesions in mouse study*, Retrieved Jan. 18, 2008, from http://www.diagnosticimaging.com/molecularimagingoutlook/2005nov/05.jhtml.

Tung, C. et al., *Preparation of a Cathepsin D Sensitive Near-Infrared Fluorescence Probe for Imaging*. Bioconjugate Chem. vol. 10, 892-896 (1999).

Shah, Khalid & Weissleder, R., *Molecular Optical Imaging: Applications Leading to the Development of Present Day Therapeutics*, NeuroRx: The Journal of the American Society for Experimental NeuroTherapeutics vol. 2, 215-225 (2005).

Tung, C. et al., *In Vivo Imaging of Proteolytic Enzyme Activity Using a Novel Molecular Reporter*. Cancer Research vol. 60, 4953-4958 (2000).

Bremer, B., et al., *Radiology, Imaging of Differential Protease Expression in Breast Cancers for Detection of Aggressive Tumor Phenotypes*, Retrieved Jan. 18, 2008, from http://radiology.rsnajnls.org/cgi/content/abstract/222/3/814.

Swain, P., et al., *Wireless capsule endoscopy*. Nature 405, vol. 417 (2000).

Gong, F. et al. *Wireless endoscopy*. Gastrointestinal Endoscopy vol. 51, No. 6, 725-729 (2000).

Marten, K. et al., *Detection of dysplastic intestinal adenomas using enzyme-sensing molecular beacons in mice*. Gastroenterolgy vol. 122, 406-414 (2002).

Massoud, T., & Gambhir, S., *Molecular imaging in living subjects: seeing fundamental biologicial processes in a new light*. Genes & Development vol. 17, 545-580 (2003).

Schulmann, K. et al., *Feasibility and Diagnostic Utility of Video Capsule Endoscopy for the Detection of Small Bowel Polyps in Patients with Hereditary Polyposis Syndromes*. American Journal of Gastroenterology vol. 100, 27-37 (2005).

Neu, B. et al., *Is Esphageal Capsule Endoscopy Feasible? Results of a Pilot*. Endoscopy vol. 35, 957-961 (2003).

Weissleder, R. et al., *In vivo imaging of tumors with protease-activated near-infrared fluorescent probes*. Nature Biotechnology vol. 17, 375-378 (1999).

Kelly, K. et al., *Detection of Invasive Colon Cancer Using a Novel, Targeted, Library-Derived Fluorescent Peptide*. Cancer Research, vol. 64, 6247-6251 (2004).

International Preliminary Report on Patentability for corresponding PCT Application No. PCT/US2006/018513 dated Nov. 22, 2007.

International Search Report for corresponding PCT Application No. PCT/US2006/18513 dated May 8, 2007.

Office Action of Israeli Patent Office for IL Patent Application No. 187335 dated Dec. 6, 2010.

European Office Action for EP 06770295.1-2319 dated Jan. 19, 2012.

Israeli Office Action for IL 187335 dated Feb. 6, 2012.

European Office Action for Application No. 06 770 295.1-1660 dated Feb. 18, 2013.

Israeli Office Action for Application No. 187335 dated May 21, 2014.

\* cited by examiner

| Targets | Sequence | | Application |
|---|---|---|---|
| Targeting Probe | | | |
| Somatostatin | DF-cyclo[CY–dW-KTC]T | (SEQ ID NO:1) | Cancer |
| Bombesin | GSGQWAVGHLM | (SEQ ID NO:2) | Cancer |
| VIP | | | Cancer |
| EGF | | | Cancer |
| Enzyme activatable probe | | | |
| Broad Cathepsins | K* | | Cancer |
| | | | Arthritis |
| | | | Atherosclerosis |
| | | | Lymphnode |
| Cathepsin B | K*K, R*R | | Cancer |
| Cathepsin K | GGPRGLPG | (SEQ ID NO:3) | Arthritis |
| Cathepsin D | GPIC(Et)F*FRLG | (SEQ ID NO:4) | Cancer |
| MMP-2 | GPLG*VRG | (SEQ ID NO:5) | Cancer |
| MMP-7 | GVPLS*LTMG | (SEQ ID NO:6) | Cancer |
| | RPLA*LWRS | (SEQ ID NO:7) | Cancer |
| uPA | GGLGQRGR*SANAILE | (SEQ ID NO:8) | Cancer |
| Caspase-1 | GWEHD*G | (SEQ ID NO:9) | Apoptosis |
| Caspase-3 | GDEVD*GSG | (SEQ ID NO:10) | Apoptosis |
| HIV | GVSQNY*PIVG | (SEQ ID NO:11) | Viral infection |
| HSV | LVLA*SSSFGY | (SEQ ID NO:12) | Viral infection |
| Cytomegalovirus protease | GVVQA*SCRLA | (SEQ ID NO:13) | Viral infection |
| Thrombin | G-dF-Pip-R*SG | (SEQ ID NO:14) | Thrombosis |
| Prostate-specific antigen | HSSKLQ* | (SEQ ID NO:15) | Cancer |
| Interleukin 1 converting enzyme | GWEHD*G | (SEQ ID NO:16) | Apoptosis |

Asterisk: proteolytic site
dW and dF: D-Trp and D-Phe, respectively
Pip: pipecolic acid
Table adapted from Tung, 2004 Biopolymers (Pept. Sci.) 76: 391-403 and Mahmood and Weissleder, 2003 Mol. Canc. Ther. 2:489-496

*FIG. 7*

CAPSULE IMAGING DEVICES, SYSTEMS AND METHODS FOR IN VIVO IMAGING APPLICATIONS

CROSS-REFERENCE TO RELATED APPLICATIONS

This non-provisional patent application claims the benefit of U.S. Provisional Application No. 60/680,580 filed May 13, 2005, and U.S. Provisional Application No. 60/742,199, filed Dec. 2, 2005, the disclosures of which are incorporated by reference herein in their entireties.

GOVERNMENT INTEREST

This invention was made with government support under Grant Nos. P30 DK 34987 and DK40247, both awarded by the National Institutes of Health. The government has certain rights in this invention.

TECHNICAL FIELD

The subject matter disclosed herein relates generally to in vivo imaging. More particularly, the subject matter disclosed herein relates to capsule imaging devices, systems and methods for in vivo imaging applications such as for gastrointestinal applications.

BACKGROUND

In the past, it has been known to use swallowable electronic capsules to collect data and transmit the data to a receiver system. Such capsules are generally known as "Heidelberg" capsules and have been used in the intestines to measure things such as pH, temperature and pressure. Other in vivo measuring systems that have been used are endoscopes, which are long tubes that a patient swallows. Endoscopes are often used to provide images of the upper or lower gastrointestinal tract, but since they typically are not very flexible and are not moved easily through small intestines, conventional endoscopes do not provide views of the small intestines. Also, endoscopes are uncomfortable, may injure a patient, and are complex to operate. Fiber-optic endoscopes utilize a fiber-optic waveguide to transmit a video signal from an area of interest to the electronics located outside of a patient's body. Video endoscopes place an electronic camera at an area of interest and transmit and store the images until after the test finishes.

Early detection of pre-malignant lesions, such as adenomatous polyps, and malignant lesions is crucial in the prevention and early treatment of common gastrointestinal cancers. With the advent of fiberoptic endoscopes such as EGD and colonoscopy whose flexibility allows an endoscopist to traverse the duodenum and the colon, lesions within the reach of the endoscope can now be detected, albeit invasively. Major portions of the small intestine, however, remain inaccessible by the conventional endoscope. In addition, fiberoptic endoscopy also has a small but significant risk of bleeding, perforation and sedation-associated cardiopulmonary incident.

Video capsule endoscopy is a minimally invasive procedure that involves swallowable camera capsules that can be used for imaging the gastrointestinal tract. Images from the video capsule can be wirelessly transmitted from the capsule to an electronic receiver outside of the body. An early example of such a video capsule is disclosed in U.S. Pat. No. 5,604,531. Such video capsules typically use white light for guidance and imaging within the gastrointestinal tract. Using conventional video capsules, however, the images generated can only indicate the presence of something, for example on an interior wall along the gastrointestinal tract. The ability to determine information such as, for example, the clinical classification of polyps such as benign (hyperplastic and lymphoid) versus pre-malignant (adenomatous) is extremely limited. Conventional video capsule endoscopy does not provide the possibility of tissue sampling, and only anatomic and morphologic information can be extracted from white light imaging.

Molecular imaging utilizing probes activated by biomarkers associated with neoplastic lesions is emerging as a powerful tool to detect and distinguish pre-malignant and malignant lesions. Such imaging involves certain molecular biomarkers such as some proteases being up-regulated in neoplastic lesions. Probes activated by these biomarkers, termed "molecular beacons", are becoming increasingly valuable tools for detecting cancerous lesions and differentiating benign and pre-malignant polyps. This new technology, utilizes special near infrared fluorescent (NIRF) imaging probes carrying non-fluorescent enzyme substrates. These are essentially undetectable after systemic administration unless locally activated by enzymes associated with disease processes. Such probes are typically injected intravenously and in vivo detection of specific enzyme activity is achieved through imaging hardware capable of detecting near-infrared light emissions. One such NIRF imaging probe used currently only in experimental animal models is based on Cathepsin B, a proteolytic enzyme that is consistently overexpressed in adenomatous polyps and cancers. In mouse models these probes have been used on dissected gastrointestinal tissue and on anesthetized mice with modified fiberoptic endoscopy. The latter application still involves invasive endoscopic methods and if applied clinically would have limitations similar to conventional endoscopy.

Accordingly, in light of the current technologies for video capsule endoscopy, significant room for improvement in the art remains for improved capsule imaging devices, systems and methods for non-invasive or less invasive in vivo imaging applications, such as for gastrointestinal applications. Improved capsule imaging devices that can distinguish and differentiate pre-malignant and malignant lesions, inflammatory lesions, and which can differentiate lesions at regions of the gastrointestinal tract not accessible by conventional endoscopic techniques are exemplary of desirable improvements.

SUMMARY

In accordance with this disclosure, novel capsule imaging devices, systems and methods are provided for in vivo imaging applications, such as for gastrointestinal applications.

It is an object of the present disclosure therefore to provide novel capsule imaging devices, systems and methods for in vivo imaging applications, such as for gastrointestinal applications. This and other objects as may become apparent from the present disclosure are achieved, at least in whole or in part, by the subject matter described herein.

BRIEF DESCRIPTION OF THE DRAWINGS

Preferred embodiments of the subject matter described herein will now be described with reference to the accompanying drawings, of which:

FIG. 7 of the drawings is a table showing exemplary targets of biological probes in accordance with the present disclosure;

DETAILED DESCRIPTION

In accordance with the present disclosure, novel capsule imaging devices, systems and methods are provided for in vivo imaging applications, such as for gastrointestinal applications. The devices, systems and methods disclosed herein integrate video capsule endoscopy and molecular imaging technology to capitalize on the minimally invasive nature of video capsule endoscopy and to provide novel techniques to determine from in vivo imaging important information such as differentiation between benign, pre-malignant and malignant lesions. The devices, systems and methods disclosed herein can have particular application for any in vivo imaging of any portion of a human or animal gastrointestinal tract and lumen, or of organs or other tissue associated with a gastrointestinal tract.

Figure 1:
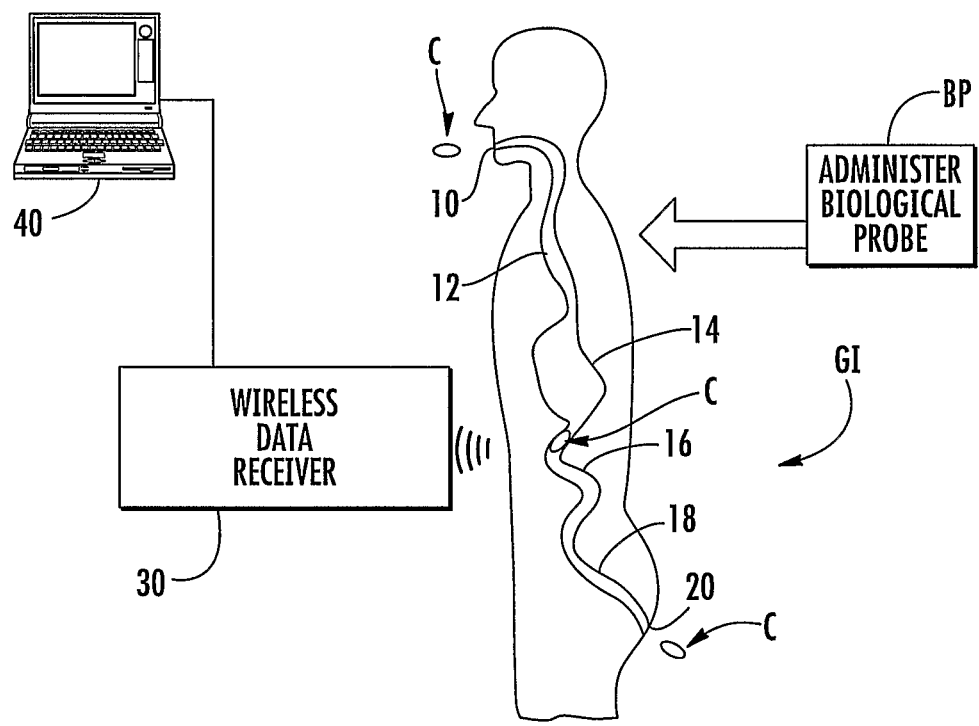
FIG. 1 of the drawings is a sectional view of a digestive tract of a human body illustrating an example of a travel path of a video imaging device in accordance with the present disclosure.

With reference to FIG. 1, video capsule endoscopy in accordance with the subject matter disclosed herein utilizes an imaging device that can be swallowed, such as for example a video imaging capsule generally designated C. Any suitably configured, sized or shaped video imaging device could be used in accordance with the present subject matter as it is not necessary for the video imaging device to be a capsule such as capsule C. As with conventional video capsule endoscopy, capsule C can be swallowed through the mouth of a patient and pass through the gastrointestinal tract generally designated GI. As shown in FIG. 1, gastrointestinal tract GI includes mouth 10, esophagus 12, stomach 14, small intestine 16, large intestine 18, and rectum 20. Once ingested into mouth 10, capsule C can travel through the complete digestive path gastrointestinal tract GI until capsule C exits gastrointestinal tract GI through rectum 20 where capsule C can be captured. While inside gastrointestinal tract GI, capsule C can capture images from within gastrointestinal tract GI at any location therein.

Once capsule C is swallowed, images can be captured as motion video or as still images, for example at a speed of two images per second. Captured images can be transmitted, to a receiver, such as receiver 30, positioned outside of the body of the patient. Images received at receiver 30 can be collected and recorded and passed to a computer, such as computer 40, where the images can be analyzed as a video or as still images. Images acquired are of excellent resolution and magnification and even allow visualization of individual villi. Prior to imaging with capsule C within gastrointestinal tract GI and in order to enable in vivo imaging in accordance with the present disclosure, a biological probe BP is administered to the patient as shown in FIG. 1 and as described later in detail. The term "biological probe" as used herein refers to any type of a probe compatible for use in biological systems, including but not limited to use in vivo.

Figure 2:
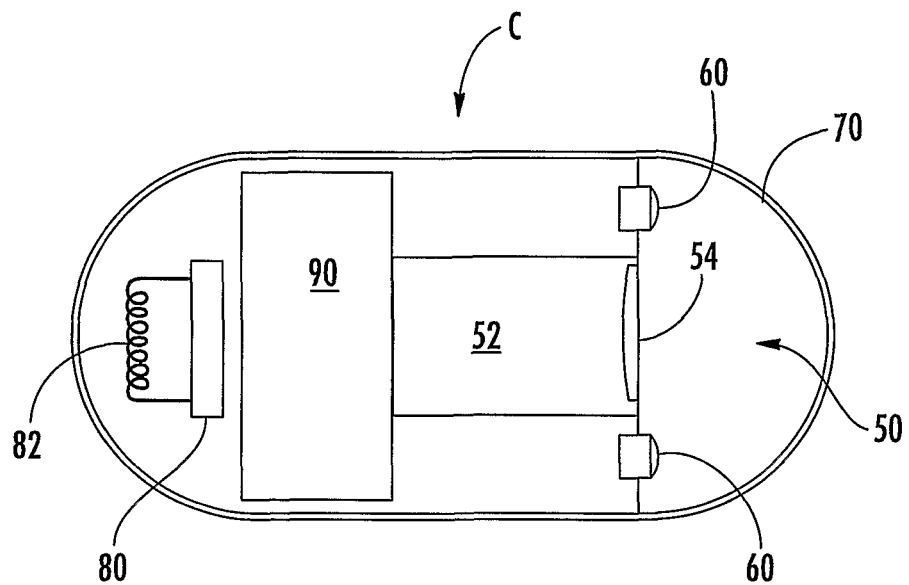
FIG. 2 of the drawings is a schematic, longitudinal cross section of one example of a conventional video imaging capsule that can be used accordance with the present disclosure.

Any type of video imaging device or capsule can be used in accordance with the presently disclosed subject matter with use of light as described herein. Video imaging capsules typically contain components therein such as, for example, an optical system including a camera, a light source for providing illumination, a transmitter for transmitting wirelessly images from the optical system, and a power source. FIG. 2 of the drawings illustrates video imaging capsule C as containing an optical system generally designated 50 that can include a camera 52 and a lens 54. A light source for providing illumination is shown for exemplary purposes only as an array of light emitting diodes (LEDs) 60 that can be positioned around lens 54. The light source can though be any suitable type of light source, such as a halogen light source or a laser light source. The light can be continuous in intensity, pulsed, or can be modulated, for example by frequency or amplitude. An optical dome 70 that can be transparent can be positioned to cover and protect lens 54 and LEDs 60 on an end of capsule C. As can be appreciated to those of skill in the art, capsule C can as desired have other configurations for its optical system, such as a configuration where camera 52 and lens 54 are positioned on or toward a side of capsule C with a side wall window instead of a dome at one or both ends of capsule C. A transmitter 80 along with an antenna 82 can wirelessly transmit images from capsule C, and a power source 90 can provide power to components within capsule C.

FIG. 2 illustrates an embodiment of imaging capsule C having one optical system 50 at one end of capsule C. However, as is known in the art, some embodiments of capsule C can further comprise a second optical system 50 at the opposite end of imaging capsule C. In these embodiments, optical systems 50 can be the same or different with regard to light transmission and imaging capabilities. For example, in some embodiments optical system 50 at one end of capsule C transmits and receives white light, whereas the opposite end optical system 50 transmits and/or receives a range of light different from the first end optical system 50, due to incorporation of one or more light filters, as disclosed in detail herein below. In some embodiments, both optical systems 50 comprise light filters that can filter light at the same or different wavelengths.

Figure 3:
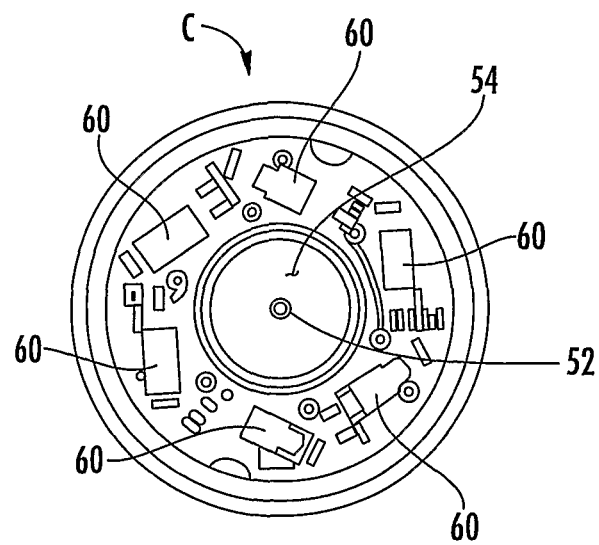
FIG. 3 of the drawings is an elevational, front end view of the video imaging capsule shown in FIG. 2 with the optical dome removed from the video imaging capsule.

FIG. 3 of the drawings further illustrates camera 52, lens 54 and LEDs 60 as and end view of capsule C is shown with dome 70 removed. LEDs 60 can be positioned as shown or in any other position for providing illumination during imaging. LEDs 60 can be white light LEDs.

In accordance with the present subject matter, a light filter can optionally be used for beneficial imaging carried out in association with an administered biological probe as described in detail further hereinbelow. The configuration of a light filter according to the present disclosure is not limited to any one particular shape or configuration as a light filter according to this disclosure can be of a variety of shapes and configurations such as, for example, the shapes and configurations described below. The light filter can be used in association with a light source as disclosed herein to provide monochromatic or substantially monochromatic near infrared light. As such, the light filter can be a bandpass light filter adapted for use with a video imaging capsule as described hereinbelow. The terms "light" and "light filter" as used herein are not intended to be limited to light emitted, filtered or received in only the visible light spectrum, but rather, the terms are inclusive of the entire electromagnetic radiation spectrum (e.g., infrared, near-infrared, ultraviolet, ultrasound, etc.), unless otherwise specifically limited, such as for example when light filters are disclosed that filter light at a particular wavelength range. In accordance with the present disclosure, however, no light filter is needed where, for example, the video imaging device is adapted for imaging using light of predetermined wavelength ranges or wavelengths. To facilitate this, the light source can be adapted for radiating light of predetermined wavelength ranges or wavelengths. For example, the LEDs could be suitably coated or otherwise adapted for emitting desired colors or a color of light by the structures used to make the LEDs such as by doping or using selected diode materials known or discovered to produce light at certain wavelengths or ranges.

Figure 4A:
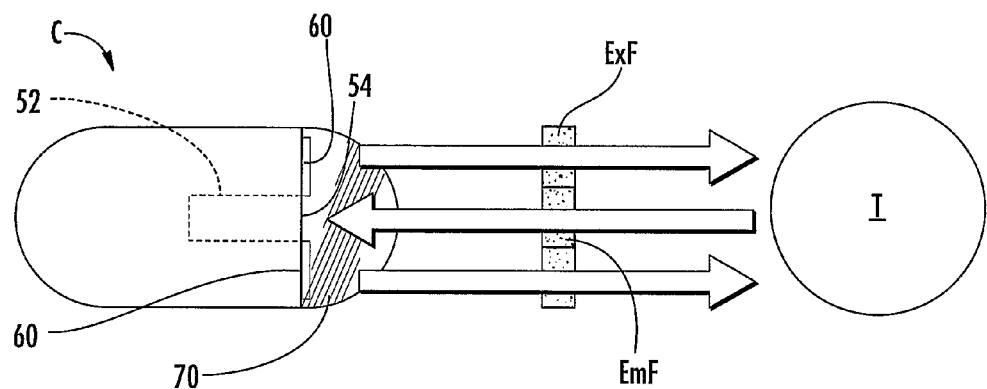
FIGS. 4A and 4B of the drawings are schematic, cross sectional illustrations of a video imaging capsule used in association with a light filter in accordance with the present disclosure.

FIG. 4A of the drawings provides a schematic illustration of video imaging capsule C used in association with a light filter generally designated F in accordance with the present disclosure where light filter F is positioned outside of capsule C. Light filter L can be any suitable type of filter made by any suitable method known now or later discovered. Light filter L can be chosen to select and allow passage of predetermined wavelengths of light, which also means light filter L can exclude passage of light outside the selected wavelengths. As shown, light L from a source such as LEDs 60 can pass through dome 70 outside of capsule C and then pass through light filter F to illuminate an imaged target T. As shown in FIG. 4A and better shown in FIG. 4C, light filter F can advantageously comprise at least one filter portion that can be an excitation filter ExF. Light filter F can also comprise at least one filter portion that can be referred to as an emission filter EmF. Light filter F can as shown in FIG. 4C be round with excitation filter ExF surrounding the centrally positioned emission filter EmF. Excitation filter ExF can be selected and used to filter light such that only light of a predetermined wavelength range is allowed passage through excitation filter ExF. As can be appreciated by those of skill in the art, the excitation light from this filtering can be light of a wavelength range suitable and desired for subsequent steps, such as for example, excitation of a component of a biological probe (e.g., a fluorochrome) as described further herein. The light source and/or camera can also be constructed to emit and receive within narrow bandwidths, without the need of an external filter or dual modality filter. For example, the LEDs can be constructed or coated to emit in the near-infrared region, such that only a single filter for the camera is required. Said filter can also be a "dynamic filter", toggling between emitting and receptive functions.

A desired wavelength range for the excitation light can be, for example and without limitation, light of near infrared wavelengths, for example from about 600 nm to about 1000 nm, as is known for use in existing optical imaging applications. When the excitation light encounters a near infrared fluorescent molecule of a biological probe as described further herein, the excitation light is absorbed by the fluorescent molecule. The fluorescent molecule then emits light that can have detectably different properties from the properties of the excitation light. Emission filter EmF can also be selected and used for filtering of light emitted from the biological probe such that only light of a predetermined wavelength range is allowed to pass through emission filter EmF. As with the excitation filter ExF, emission filter EmF can be selected and used to filter light such that only light of a predetermined wavelength range is allowed passage therethrough, resulting in emission light within a predetermined wavelength range that can be desirably different from the wavelength range of the excitation light. For example, and without limitation, a desired wavelength range for excitation light can also be from about 600 nm to about 1000 nm. Light filter F can be used in association with capsule C such that excitation filter ExF filters light L emitted from LEDs 60 and going to target T, while emission filter EmF filters light L returning from target T to camera 52, which may or may not include lens 54. Differences in the wavelengths of light traveling in a direction through excitation filter ExF and in an opposite direction through emission filter EmF can facilitate providing a contrast to the imaging produced by a video imaging capsule.

As discussed in detail below, target T can comprise targeted tissue within a gastrointestinal tract, and the targeted tissue can comprise a previously administered biological probe that has been absorbed by target T. In some embodiments, the probe is an activatable probe, which can be activated by a component of target T. Light L passed through light filter F and to target T can then excite the absorbed and activated probe and can cause the probe to emit light L from target tissue T that can pass back through light filter F to camera 52. This can occur, for example, when excitation light within a desired or particular wavelength range contacts a fluorescent molecule of the absorbed and activated probe, resulting in excitation of the fluorescent molecule and transmission by the molecule of emission light at a different wavelength than the excitation light that contacted the fluorescent molecule.

Figure 4B:
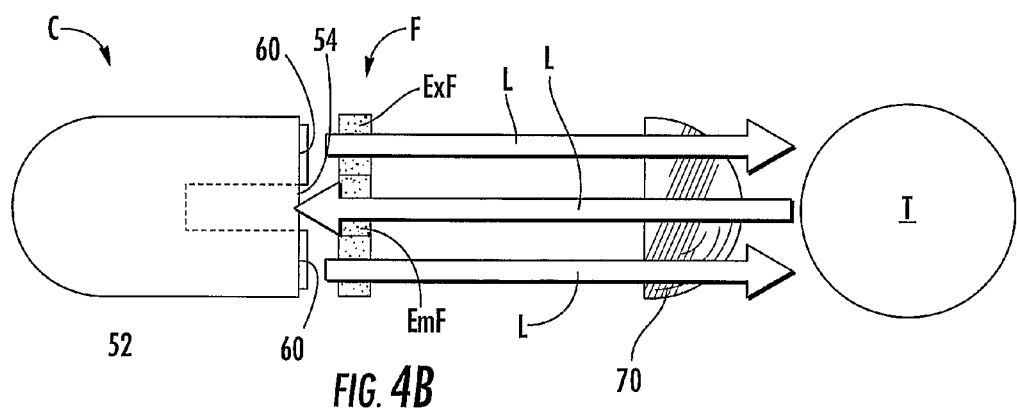
Figure 4C:
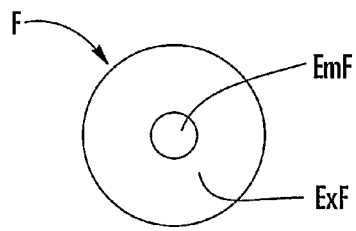
FIG. 4C of the drawings is an elevational front view of a light filter that can be used in accordance with the present disclosure.

In accordance with another aspect, light filter F can be as described above but be positioned within capsule C as illustrated for example in FIG. 4B of the drawings. In this configuration, light filter L can be a wafer that can be round and comprise at least an excitation filter ExF and can also comprise an emission filter EmF as described above and shown for example and without limitation in FIG. 4C.

Figure 5A:
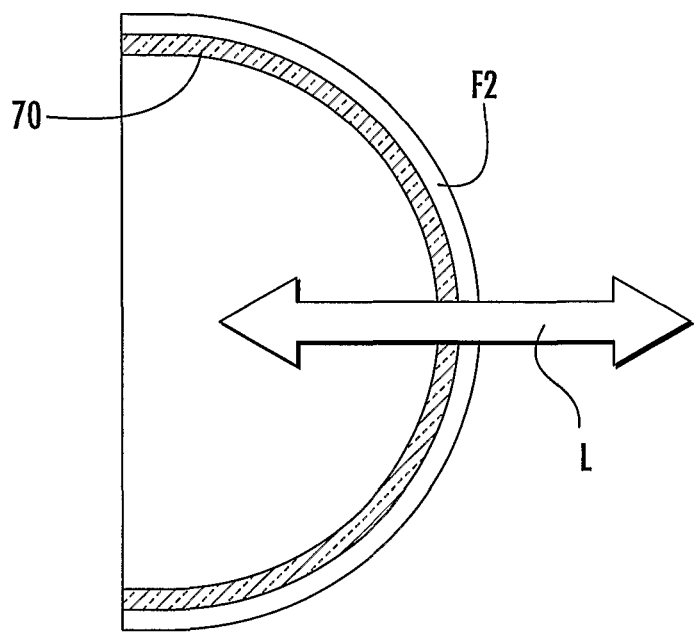
FIGS. 5A, 5B and 5C of the drawings are cross sectional illustrations of a video imaging capsule dome showing different configurations of a light filter placed thereon in accordance with aspects the present disclosure.
Figure 5B:
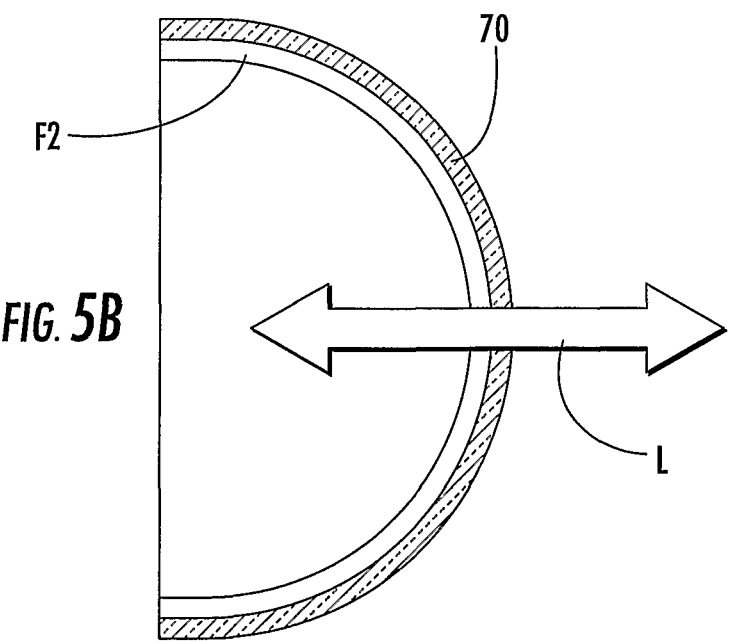
Figure 5C:
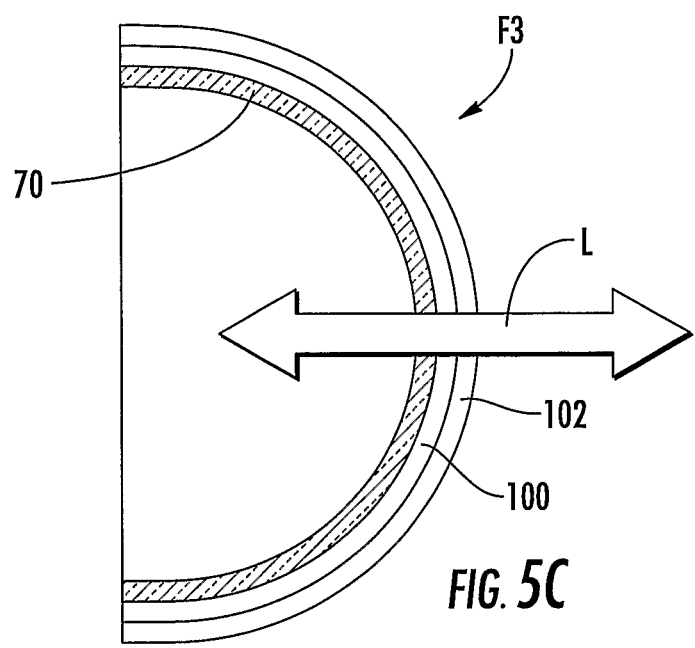
Figure 6:
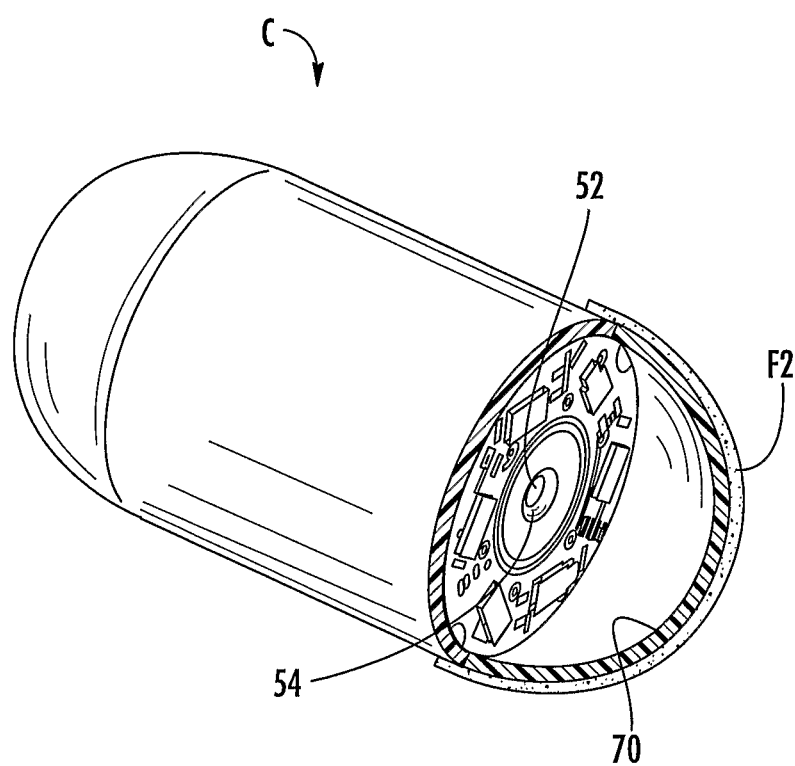
FIG. 6 of the drawings is a perspective view of a video imaging capsule that can be used in accordance with the present disclosure showing a portion of the dome cut away for illustration purposes.

FIGS. 5A, 5B and 5C of the drawings illustrate other examples of light filters that can be used in accordance with the presently disclosed subject matter. In each of FIGS. 5A, 5B and 5C, the light filter is shown as a filter layer placed onto dome 70 of a video imaging capsule. To assist in understanding FIGS. 5A, 5B and 5C, FIG. 6 of the drawings provides a perspective view of capsule C illustrating how capsule C can have a light filter F2 as a layer on the outside of dome 70. A portion of dome 70 is shown cut away for illustration purposes to better show LEDs 60 and lens 54 of camera 52.

As shown in FIG. 5A, light filter F2 can be positioned as a single outer layer attached to and on the outside of dome 70. Light L can pass through and be filtered by light filter F2. As shown in FIG. 5B, light filter F2 can be positioned as a single inner layer attached to and on the inside of dome 70. A single layer can be used either on an interior surface of capsule C, such as inside dome 70 as shown in FIG. 5A, or on an exterior surface of capsule C, such as an exterior of dome 70 as shown in FIG. 5B. Where a single layer is used, light filter F2 can comprise both an excitation filter ExF and an emission filter EmF, just an excitation filter ExF, or just an emission filter EmF.

As shown in FIG. 5C, light filter generally designated F3 can comprise a plurality of layers such as, for example, layers 100 and 102 as light filter F3 can be positioned on either side of dome 70, such as for example attached to and on the outside of dome 70 as shown. Dome 70 can be coated with filter layers 100 and 102, which can be two different filters. For example, layer 100 could be an excitation filter and layer 102 could be an emission filter. The two filters could be coated sequentially (on top of each other) or formed so as to create a single layer. For each filter layer 100 and 102, light is filtered only when it passes through the filter layer one in unidirectional way. Also, each filter layer 100 and 102 can allow predetermined wavelengths of light to pass through in the one direction of filtering, while preventing wavelengths of light not in the predetermined range that may try to pass through in the one filtering direction. The wavelength ranges can be different for filter layers 100 and 102. For example, where layer 100 is an excitation filter, light from a source inside the capsule can be filtered in one direction by and through filter layer 100 to allow passage therethrough only of light with a predetermined and specific excitation wavelength. Similarly, where layer 102 is an emission filter, light traveling from outside and toward the capsule can be filtered in an opposite direction by and through filter layer 102 to allow passage therethrough only of light with a different, predetermined and specific emission wavelength. It is also envisioned that light filters could be attached as layers on opposite sides of dome 70. In each of the configurations shown in FIGS. 5A, 5B and 5C, light filters F2 and F3 can be applied by any suitable techniques known now or in the future, such as, for example, by spray coating dome 70.

As noted herein above, imaging of tissue of interest (i.e., "target tissue") can be enhanced using a biological probe comprising fluorescent molecules (e.g., fluorochromes) that can accumulate in and enhance visualization of the tissue of interest. The presently disclosed subject matter encompasses utilizing a biological probe to enhance visualization of tissue of interest as well as utilizing two or more biological probes, either at the same time or sequentially, whose optical properties can be distinguishable from those of the others. The presently disclosed subject matter therefore provides for the imaging of multiple events or targets simultaneously.

The term "target tissue" as used herein refers to not only a group of cells organized to perform a particular function as "tissue" is used in the traditional sense, but also can individual cells, organs, and non-cellular biological material associated with cells, tissues, and/or organs. The contents of the lumen of the gastrointestinal tract are also included.

As can be appreciated by those of skill in the art, a "fluorochrome" of a biological probe can include, but is not limited to, a fluorochrome, a fluorophore, a fluorochrome quencher molecule, or any organic or inorganic dye. In some embodiments, the fluorochromes can be red and near infrared fluorochromes (NIRFs) with absorption and emission maximum between 600 and 1300 nm. Preferred fluorochromes can have (1) high chemical and photostability, (2) non-toxicity, (3) good biocompatibility, biodegradability and excretability, and (4) commercial viability and scalable production for large quantities (i.e., gram and kilogram quantities) required for in vivo and human use. Methods for measuring these parameters are known to one of skill in the art.

In some aspects of the present disclosure, a fluorochrome can be specifically selected based on a substantial difference between its excitation and emission wavelengths. In these embodiments, the fluorochrome can function as both an imaging and as a therapeutic agent. The energy difference between the excitation light and the emission light wavelengths can be released from the fluorochrome in the form of heat. As a biological probe is localized to target tissue of interest initially to visualize the target tissue, the heat released will dissipate into the target tissue. A fluorochrome can be specifically selected to maximize the difference between the excitation light and the emission light wavelengths in order to maximize the heat generated and delivered to the target tissue, thereby shrinking and even killing the target tissue with minimal or no damage to peripheral tissue. Thus, in instances where the target tissue comprises a suspected cancer, the biological probe can be utilized to identify and quantify the presence of cancerous tissue. In addition, simultaneously or sequentially thereafter the probe can therapeutically treat the target by killing the cancerous tissue through the heat generated from fluorescence of the probe.

Fluorochromes that can be utilized with the presently disclosed subject matter include for example, but are not limited to, fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3, 3.5, 5, 5.5, and 7; phycoerythrin; phycoerythrin-Cy conjugates; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives (e.g., hydroxycoumarin, aminocoumarin, and methoxycoumarin); pyrenes; pyridyloxazole derivatives; dapoxyl dyes; Cascade Blue and Yellow dyes; benzofuran isothiocyanates; sodium tetrafluorophenols; 4,4-difluoro-4-bora-3a,4a-diazas-indacene; Alexa fluors (e.g., Alexa fluors 350, 430, 488, 532, 546, 555, 568, 594, 633, 647, 660, 680, 700, and 750); green fluorescent protein; and yellow fluorescent protein. The peak excitation and emission light wavelengths will vary for these compounds and selection of a particular fluorochrome for a particular application can be made in part based on excitation and/or emission light wavelengths.

Fluorochromes that can be used to construct biological probes are also described in U.S. Pat. Application No. 2002/0064794, PCT Publication No. WO 02/24815, U.S. Pat. Nos. 5,800,995, 6,027,709, PCT Publication No. WO 00/53678, PCT Publication No. WO 01/90253, EP 1273584, U.S. Patent Application No. 2002/0115862, EP 1065250, EP1211294, EP 1223197, PCT Publication No. WO 97/13810, U.S. Pat. Nos. 6,136,612, 5,268,486, 5,569,587, and Lin et al., 2002 Bioconj. Chem. 13:605-610, the entire teachings of which are incorporated herein by reference.

In some embodiments, a biological probe can comprise a targeting moiety to facilitate accumulation of the probe at or within the target tissue. As such, a "targeting moiety" can be any moiety that can be chemically linked to the biological probe of the present subject matter that enhances accumulation, targeting, binding, recognition, metabolic activity of the probe, or enhances the efficacy of the probe in any manner. This can include, but is not limited to, membrane (or transmembrane) translocation signal sequences, which could be derived from a number of sources including, without limitation, viruses and bacteria. Also included are moieties such as monoclonal antibodies (or antigen-binding antibody fragments, such as single chain antibodies) directed against a target-specific marker, a receptor-binding polypeptide directed to a target-specific receptor, a receptor-binding polysaccharide directed against a target-specific receptor and other molecules that target internalizing receptors, including but not limited to, nerve growth factor, oxytocin, bombesin, calcitonin, arginine vasopressin, angiotensin II, atrial natriuretic peptide, insulin, glucagons and glucagon-like peptides, prolactin, gonadotropin, and various opioids. Non-limiting examples of biological probes incorporating targeting moieties are disclosed in FIG. 7 under "Targeting probe" as well as in Tung, 2004 Biopolymers (Pept. Sci.) 76: 391-403, herein incorporated by reference in its entirety.

As previously noted, in some embodiments the biological probe can be activatable, where the probe in its native state has little or no fluorescence emission, due to for example intramolecular quenching, and detection of the probe is not possible until it has been activated or metabolized. For example, the biological probe can become activated only after being targeted to a desired tissue due to a particular unique characteristic of the target tissue. In embodiments where the probe is activatable, the probe can further comprise a targeting moiety to increase accumulation of the probe within the target tissue. A targeting moiety, however, can be unnecessary in some embodiments where the probe is activatable, as the activation of the probe only within the target tissue may be sufficient to distinguish the target tissue from surrounding tissues.

Intramolecular fluorescence quenching by non-activated probes can occur by any of various quenching mechanisms. Several mechanisms are known, including resonance energy transfer between two fluorochromes. In this mechanism, the emission spectrum of a first fluorochrome should be very similar to the excitation of a second fluorochrome, which is in close proximity to the first fluorochrome. Efficiency of energy transfer is inversely proportional to $r^6$, where r is the distance between the quenched chromophore and excited chromophore. Self-quenching can also result from fluorochrome aggregation or excimer formation. This effect is strictly concentration dependent. Quenching also can result from a non-polar-to-polar environmental change.

To achieve intramolecular quenching, several strategies can be applied. They include: (1) linking a second fluorochrome, as an energy acceptor, at a suitable distance from the first fluorochrome; (2) linking fluorochromes to a backbone molecule at high density, to induce self-quenching; and (3) linking polar fluorochromes in a vicinity of non polar structural elements of a backbone and/or protective chains. Fluorescence is partially or fully recovered upon cleavage of the fluorochrome from neighboring fluorochromes and/or from a particular region, e.g., a non-polar region, of the probe.

In some embodiments, the activatable biological probe can be activated through the catalytic activity of an enzyme expressed in the target tissue, either uniquely or in significantly increased amounts as compared to non-target tissue. For example, in some embodiments the biological probe can be activated by a protease expressed by a target tissue.

Proteases represent a number of families of proteolytic enzymes that catalytically hydrolyze peptide bonds. A particular protease, however, will not cleave every peptide bond in a protein. Rather, the proteases are specific to particular amino acid sequences that serve as recognition domains for each particular protease. Principal groups of proteases can include metalloproteases, serine proteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused by and can be characterized by alterations in the activity of specific proteases and their inhibitors. For example, emphysema, arthritis, thrombosis, cancer and some forms of hemophilia result from the lack of regulation of serine protease activities (see, for example, Textbook of Biochemistry with Clinical Correlations, John Wiley and Sons, Inc. N.Y. (1993)).

Also for example, proteases have been implicated in cancer metastasis. Increased synthesis of the protease urokinase has been correlated with an increased ability to metastasize in many cancers. Urokinase activates plasmin from plasminogen which is ubiquitously located in the extracellular space, and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. Adv. Cancer. Res., 44: 139 (1985).

Cathepsin B and cathepsin H protease activities have also been used to detect submillimeter sized tumors using NIR fluorescent probes. In addition, cathepsin D-positive tumors have also been imaged in mouse models.

Similar to cathepsins, matrix metalloproteinases (MMPs) are overexpressed in a number of tumors and in inflamed tissue. The level of their expression has been shown to be directly related to the tumor stage and metastasis. A number of different MMP inhibitors (e.g., AG 3340), which act as cytostatic and anti-angiogenic agents and some of which are in clinical trials have been developed.

As such, measurement of changes in the activity of specific proteases is clinically significant in the detection and treatment of the underlying disease states. Thus, biological probes can be targeted to tissue of interest based on the differentiating proteases, which can specifically target and activate the probes.

In some embodiments of protease-activated biological probes of the presently disclosed subject matter, the probe can comprise a fluorochrome linked to an "acceptor" molecule by a backbone. The backbone can be any biocompatible polymer. For example, it can be a polypeptide, a polysaccharide, a nucleic acid, or a synthetic polymer. Polypeptides useful as a backbone can include, for example, protease peptide recognition sequences (e.g., poly-lysine), albumins, and antibodies. The backbone also can be a synthetic polymer such as polyglycolic acid, polylactic acid, poly(glycolic-colactic) acid, polydioxanone, polyvalerolactone, poly-.epsilon.-caprolactone, poly(3-hydroxybutyrate, poly(3-hydroxyvalerate) polytartronic acid, and poly(β-malonic acid). In some embodiments, the backbone can be a peptide having an amino acid sequence that can be recognized and cleaved by a particular protease. The donor fluorochrome typically is excited by incident radiation at a particular wavelength which it then re-emits at a different (longer) wavelength. When the fluorochrome is held in close proximity to the acceptor molecule, the acceptor absorbs the light re-emitted by the fluorophore thereby quenching the fluorescence signal of the donor molecule. The acceptor can be a fluorescent or non-fluorescent molecule. If the acceptor is a fluorescent molecule, the acceptor and the fluorochrome can be the same molecules that quench each other when in close proximity, but can fluoresce when separated. Cleavage of the peptide joining the fluorochrome and the acceptor by the targeted protease results in separation of the two molecules, release of the quenching effect and increase in fluorescence.

In some embodiments, the biological probe further comprises protective molecules. Suitable protective molecules include polyethylene glycol, methoxypolyethylene glycol, methoxypolypropylene glycol, copolymers of polyethylene glycol and methoxypolypropylene glycol, dextran, and polylactic-polyglycolic acid. The protective molecules can be included in some embodiments to decrease the immunogenicity of the biological probe, increase plasma half-life, and, in some embodiments, facilitate cell internalization.

Figure 8:
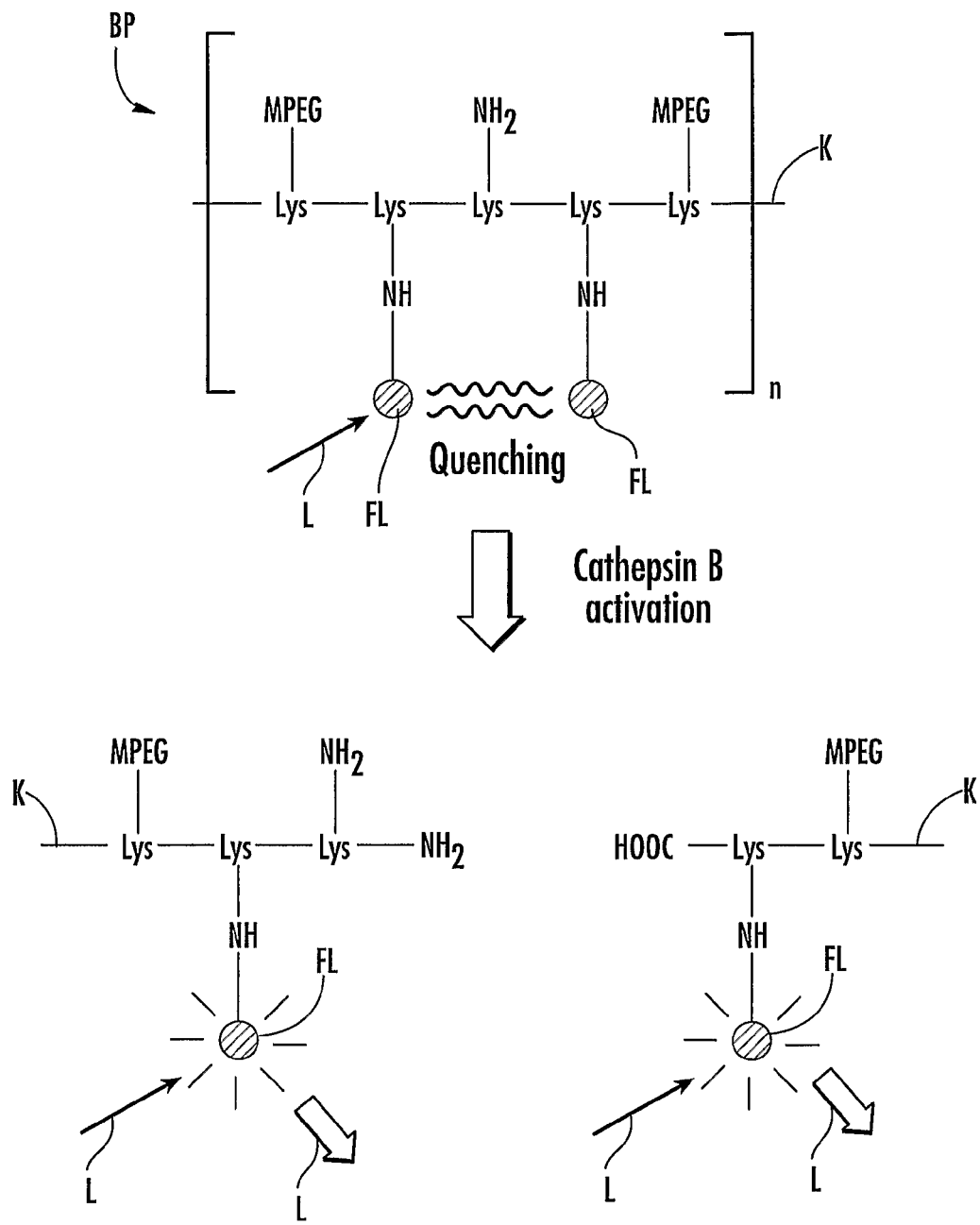
FIG. 8 of the drawings is a schematic view of an exemplary activatable biological probe showing activation of the probe by targeted enzymatic cleavage in accordance with the present disclosure.

FIG. 8 shows an exemplary biological probe BP comprising a poly-lysine peptide K backbone having fluorochromes FL and a protecting substrate of methoxyl polyethylene glycol (MPEG) linked thereto. Poly-lysine peptide K is a substrate for the protease cathepsin B, increased expression of which has been demonstrated to occur in particular cancers. As shown in FIG. 8, fluorochromes FL quench each other due to close proximity. When, however, a biological probe BP contacts a cathepsin B molecule, such as within a cancerous tissue, the cathepsin B cleaves poly-lysine peptide K, thereby releasing fluorochromes FL from close proximity and permitting excitation and fluorescence of fluorochromes FL when struck with light at the excitation wavelength of fluorochromes FL. The fluorescence then distinguishes a cancerous target tissue from surrounding normal tissue.

Any amino acid sequence that comprises a recognition domain and can thus be recognized and cleaved by a protease is suitable for the "protease binding site" of the biological molecules of the presently disclosed subject matter. Known protease substrate sequences and peptide inhibitors of proteases possess amino acid sequences that are recognized by the specific protease they are cleaved by or that they inhibit. Thus known substrate and inhibitor sequences provide the basic sequences suitable for use in the protease recognition region. A number of proteases and their substrate sequences suitable for use as protease binding domains in the compositions of the presently disclosed subject matter are indicated in FIG. 7 under "Enzyme activatable probe" and in Tung, 2004 Biopolymers (Pept. Sci.) 76: 391-403 and Mahmood and Weissleder, 2003 Mol. Canc. Ther. 2:489-496, both of which are herein incorporated by reference in their entireties. One of skill will appreciate that this is not a complete list and that other protease substrates can be used as well.

The fluorochromes can be linked to the peptide backbone by any of a number of means well known to those of skill in the art. In one embodiment, the fluorochrome can be linked directly from a reactive site on the fluorochrome to a reactive group on the peptide such as a terminal amino or carboxyl group, or to a reactive group on an amino acid side chain such as a sulfur, an amino, or a carboxyl moiety. Many fluorochromes normally contain suitable reactive sites. Alternatively, the fluorochromes can be derivatized to provide reactive sites for linkage to another molecule. Fluorochromes derivatized with functional groups for coupling to a second molecule are commercially available from a variety of sources. The derivatization can be by a simple substitution of a group on the fluorochrome itself, or may be by conjugation to a linker.

Suitable linkers are well known to those of skill in the art and include, but are not limited to, straight or branched-chain carbon linkers, heterocyclic carbon linkers, or peptide linkers. The linkers may be joined to the carboxyl and amino terminal amino acids through their side groups (e.g., through a disulfide linkage to cysteine).

Particularly preferred linkers are capable of forming covalent bonds to amino groups, carboxyl groups, or sulfhydryl. Amino-binding linkers include reactive groups such as carboxyl groups, isocyanates, isothiocyanates, esters, haloalkyls, and the like. Carboxyl-binding linkers are capable of forming include reactive groups such as various amines, hydroxyls and the like. Finally, sulfhydryl-binding linkers include reactive groups such as sulfhydryl groups, acrylates, isothiocyanates, isocyanates and the like. Particular exemplary linkers include sulfoMBS (m-maleimidobenzoyl-N-hydroxysulfosuccinimide ester) for linking amino groups (e.g. an amino group found on a lysine residue in the peptide) with sulfhydryl groups found on the solid support, or vice versa, for linking sulfhydryl groups (e.g. found on a cysteine residue of the peptide) with amino groups found on the solid support. Other exemplary linkers can include EDC (1-ethyl-3-(3-dimethylaminopropryl)-carbodiimide) and bis-(sulfosuccinimidyl suberate). Additional suitable linkers are well known to those of skill in the art.

In another embodiment of the presently disclosed subject matter, the biological probes can be manufactured into an acceptable pharmaceutical formulation.

Pharmaceutically acceptable carriers, adjuvants, and vehicles may be used in the composition or pharmaceutical formulation of the present subject matter. Included carriers, adjuvants, or and vehicles can include, but are not limited to, ion exchangers, alumina, aluminum stearate, lecithin, serum proteins such as albumin, buffer substances such as phosphate, glycine, sorbic acid, potassium sorbate, TRIS (tris (hydroxymethyl)amino methane), partial glyceride mixtures of fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polypropylene block polymers, sugars such as glucose, and suitable cryoprotectants.

The pharmaceutical compositions of the presently disclosed subject matter can be in the form of a sterile injectable preparation. This preparation can be prepared by those skilled in the art of such preparations according to techniques known in the art. The possible vehicles or solvents that can be used to make injectable preparations include water, Ringer's solution, and isotonic sodium chloride solution, and D5W. In addition, oils such as mono- or diglycerides and fatty acids such as oleic acid and its derivatives can be used. The pharmaceutical compositions of the present subject matter can also be in the form of a salt.

The formulation of a probe can also include an antioxidant or some other chemical compound that can prevent or reduce the degradation of the baseline fluorescence, or preserve the fluorescence properties, including, but not limited to, quantum yield, fluorescence lifetime, and excitation and emission wavelengths. These antioxidants or other chemical compounds can include, but are not limited to, melatonin, dithiothreitol (dTT), defroxamine (DFX), methionine, DMSO, and N-acetyl cysteine.

The probes and pharmaceutical compositions of the presently disclosed subject matter can be administered orally, parentally, by inhalation, topically, rectally, nasally, buccally, vaginally, or via an implanted reservoir. The term "parental administration" includes intravenous, intramuscular, subcutaneous, intraarterial, intraarticular, intra synovial, intrasternal, intrathecal, intraperitoneal, intracisternal, intrahepatic, intralesional, intracranial and intralymphatic injection or infusion techniques. The probes can also be administered via catheters or through a needle to any tissue.

Figure 9:
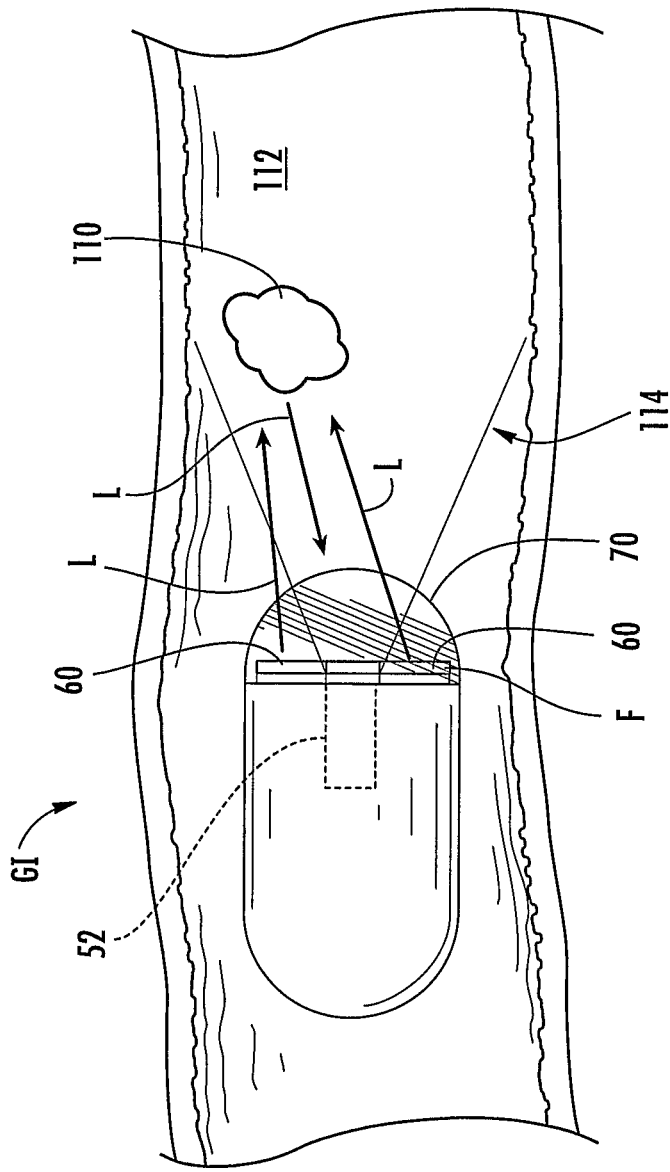
FIG. 9 of the drawings is a perspective view in partial cutaway illustrating imaging by a video imaging capsule used in association with a light filter and probe in accordance with the present disclosure.

FIG. 9 of the drawings is a perspective view in partial cutaway illustrating imaging within a portion of a gastrointestinal tract GI by a video imaging capsule C having a light filter F that has been positioned within capsule C. It can be understood therefore that imaging can occur in accordance with this disclosure after a suitable probe has been administered as described above. A target tissue here within gastrointestinal tract GI is shown as target tissue 110 that has grown on the inside surface or wall 112 of gastrointestinal tract GI. Camera 52 has a field of view, generally represented as view 114, through dome 70 as illuminated by light from LEDs 60 within capsule C. Based upon the type of biological probe used, target tissue 110 for illustration purposes here has already absorbed the previously administered probe. Light L can be emitted from LEDs 60 and pass through light filter F toward target tissue 110. Light filter F only allows passage therethrough of a predetermined wavelength or wavelength range of light L coming from LEDs 60. Light L as filtered by light filter F is the excitation light at a desired, excitation wavelength that can contact the biological probe absorbed by target tissue 110. Contact of the biological probe by the excitation light can excite the fluorochrome of the probe that has been absorbed (and if an activatable probe, also activated by target tissue 110) to fluoresce and emit light back toward capsule C, wherein the emitted light can be of a different wavelength range than the wavelength or wavelength range of the excitation light. The emitted light from target tissue 110 can be filtered by light filter F so that only emitted light of a predetermined wavelength or wavelength range can be allowed to pass through light filter F. While not necessary according to this disclosure, this filtering of the emitted light can help improve the signal to noise ratio.

Figure 10A:
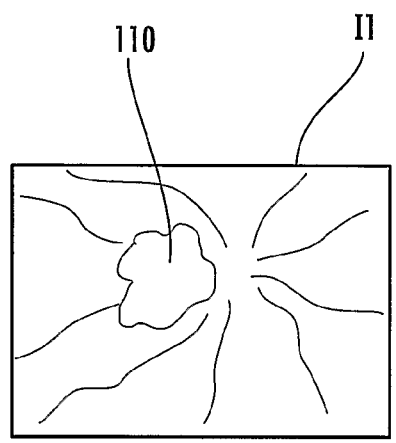
FIGS. 10A and 10B of the drawings are schematic illustrations of images produced from the video imaging capsule used in FIG. 9 with and without a light filter and probe in accordance with the present disclosure.
Figure 10B:
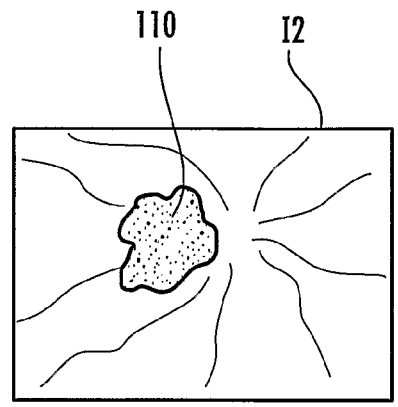

FIGS. 10A and 10B of the drawings are illustrative images 11 and 12, respectively, transmitted and displayed, such as on a computer display, from video imaging capsule C shown in FIG. 9 with and without, respectively, a light filter and probe in accordance with the present disclosure. Image 11 in FIG. 10A illustrates a white light only image that can be generated by using capsule C without a light filter and probe as disclosed herein. A physician can determine from such white light imaging that target tissue 110 is there, but no determination can be made as to what target tissue 110 is or how advanced its growth may be. Image 12 in FIG. 10B illustrates an image that can be generated by using capsule C along with a light filter and activatable probe as disclosed herein. Using a light filter and probe, it can be determined if target tissue 110 is in fact a type of tissue that has been targeted for based upon use of different probes. For example, intestinal benign, pre-malignant, and malignant tissues can be differentiated.

The specific measurement of signal intensity by standard digital imaging techniques may or may not be incorporated to improve or confirm tissue differentiation and quantitation. For example, differences in signal intensity emitted from an activated probe can be measured. The differences in signal intensity can be due to differences in concentration of accumulated probe or differences in activation of the probe. Accumulation or activation differences, depending on the probe utilized, can be indicative of the presence and severity of a particular disorder. For example, it has been demonstrated that cathepsin B is expressed at a higher concentration in malignant lesions compared to premalignant lesions and the concentration in premalignant lesions is much higher than normal tissue. A probe specifically activated by cathepsin B will therefore be activated at greater quantities in malignant lesions than in premalignant lesions or normal tissue, resulting in greater signal intensity from malignant lesions, which can be quantitated. Because of the ability to quantify, one can thus differentiate a cancerous lesion from a pre-cancerous lesion. As another example, imaging probes specific to inflammatory components are activated and emit at a measurable signal intensity based on how intense an inflammatory response is within a target tissue, thereby permitting quantitation of inflammation within the target tissue. Quantitation of inflammation is, for example, applicable in the diagnosis and measurement of inflammatory bowel disease. Further, probes designed to be activated by particular enzymes that are up-regulated in inflammatory lesions and not pre-malignant lesions would have the capability to distinguish inflammation from pre-malignant lesions. As another example, a probe specific for a particular microorganism (see FIG. 7) can be utilized to determine not only whether infection by the organism exists, but also by quantifying the intensity of the probe signal, determine the extent of infection. With the ability to quantitatively determine the extent of presence of a microorganism, one can identify whether a GI disease is truly associated with the specific microorganism or not (e.g., if detected at a high concentration, yet found in the presence of a normal GI tract, the microorganism is unlikely a pathogen).

Other GI tract lesions which can be diagnosed and treated include, but are not limited to, inflammation (e.g., Crohn's disease) and vascular lesions (e.g., vascular ectasias).

EXAMPLES

Capsule endoscopy (CE) is a minimally invasive technology designed to image the GI tract, such as the stomach and small intestine. The ability of the current white-light CE imaging to discriminate different types of normal and diseased tissues (e.g., different types of polyps) is limited. Molecular imaging utilizing probes activated by neoplasm biomarkers, such as protease activated Near Infrared Fluorescent (NIRF) probes, is a potentially powerful tool to detect and distinguish premalignant and malignant lesions. In these Examples, it was tested whether CE could be integrated with biological probes (e.g., NIRF probes) to detect premalignant lesions.

The following Examples provide illustrative embodiments. Certain aspects of the following Examples are disclosed in terms of techniques and procedures found or contemplated by the present inventors to work well in the practice of the embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Figure 11:
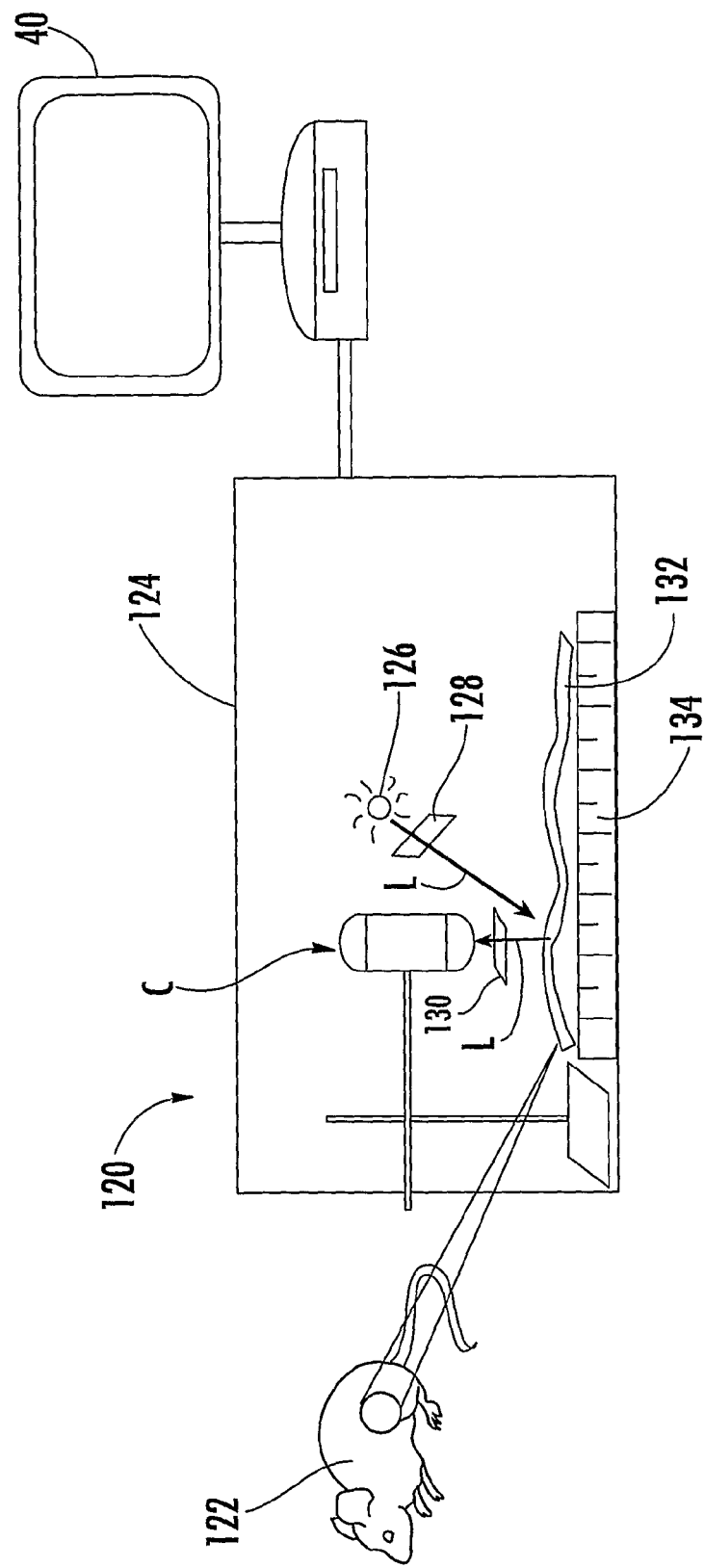
FIG. 11 of the drawings is a schematic illustration of an example of video imaging using a light filter and probe in accordance with the present disclosure.

Benign and Adenomatous Polyps Distinguished Using CE Coupled with an Activatable Probe To verify the efficacy of a Cathepsin B probe in distinguishing benign versus dysplastic adenoma, four mouse models were employed with a NIRF imaging system 120, as shown in FIG. 11. Apc$^{Min/+}$ mice spontaneously generate tumors and were used as a model for multiple adenomas in the small and large intestine. Aged GH-TG mice develop benign polyps (hyperplastic and lymphoid) and were used as negative controls.

Mice (exemplified as mouse 122 in FIG. 11) of appropriate age were anesthetized with 90 mg/kg ketamine and 10 mg/kg xylazine intraperitoneally and then administered a Cathepsin B probe (PROSENSE™ 680 (VisEN Medical, Inc., Boston, Mass., U.S.A.) intravenously via tail vein injection at a dose of 2 nmol Cy 5.5 per animal. Animals were then sacrificed 24 hours after the Cathepsin B injection. The entire bowel of the $Apc^{Min/+}$, GH-TG and wild type mice were removed for NIRF imaging.

NIRF imaging system 120 was comprised of a light-tight chamber 124 equipped with a 150-watt halogen white light source 126, an excitation filter system (610-650 nm) 128, a capsule imaging device C and an emission bandpass filter 130 to detect fluorescence (Cy 5.5 680-720 nm). Images were acquired over 3 minutes, transmitted to a computer 40, and analyzed using commercially available software.

Tissue samples 132 were obtained from the entirety of each polyp and from adjacent size-matched normal gastrointestinal mucosa in the polyp/tumor mouse models. Tissue samples 132 were likewise obtained from comparable regions of normal mucosa of wild-type mice. Mean signal intensities (SI) were recorded and the target (adenoma) to background (mucosa) contrast (TBC) was calculated as follows: TBC(%)= $([SI_{adenoma}-SI_{mucosa}]/SI_{mucosa}) \times 100$. A fluorescent ruler 134 placed along the side of a sample served as a landmark reference for correlating images collected to specific regions of sample 132.

Polyps within the same animal were resected after completion of all experiments and separated into two groups based on TBC values, with a higher TBC suggestive of adenomatous lesions. The polyps underwent further histopathology analysis to confirm the polyp types.

The molecular imaging of the polypoid lesions was further verified by a standard NIRF detecting device, such as an IVIS® Imaging System (Xenogen, Alameda, Calif. U.S.A.). In addition, positive and negative controls were imaged with CE using PROSENSE™ 680 samples added to buffer with and without trypsin on glass slides.

NIRF images of polypoid lesions in the intestine of $Apc^{Min/+}$ mice were readily visualized by CE molecular imaging. White-light images obtained by CE through light-tight chamber 124 were similar in quality to those from human applications. NIRF images captured by CE revealed discrete light spots on the control slides only in solutions with trypsin.

The present data demonstrate successful detection of polypoid lesions with CE under near infrared light using a molecular probe specific for neoplastic intestinal lesions. Thus, molecular imaging with capsule endoscopy, as disclosed by the presently disclosed subject matter, can provide a novel approach for detecting premalignant and malignant lesions in the GI tract.

Example 2

Detection of Polypoid Lesions in Mouse GI Using a White Light Capsule Imaging Device To test the feasibility of detecting polypoid lesions in mouse GI tract by visible light CE (VCE), the following experiment was carried out under white light conditions. Equipped with two identical sensors, the PILLCAM ESO® (Given Imaging, Yoqneam, Israel) is a twin-camera video capsule that transmits antegrade and retrograde images simultaneously. In light-tight chamber 124 shown in FIG. 11, the PillCAM ESO® was moved mechanically along the dissected murine intestine or stomach (described in Example 1) with one sensor of the capsule focused on the dissected tissue to capture all polypoid lesions under white light. Images captured by the sensor facing the dissected GI tract were transmitted to the recorder via sensor arrays attached outside the light chamber. A sensor at the other end of capsule was turned off for this experiment. The video was reviewed as slowly as one frame at a time and the total number of polypoid lesions counted. The number of polypoid lesions obtained from the video was then compared with the number of polypoid lesions obtained by manual counting. The data from both counting methods matched, indicating lesions can be identified by video imaging.

Example 3

Detection of Polypoid Lesions in Mouse GI Using a Capsule Imaging Device Having NIRF Transmitting and Imaging Capabilities In light-tight chamber 124, a 150-watt halogen white light source coupled with excitation bandpass filter (610-650 nm) was used for excitation and the commercially available PillCAM ESO® with emission bandpass filter (680-720 nm) was placed in front of one of the optical domes and used for emission detection. This approach served as a proof of principle without the necessity of modifying the optical dome directly. However, in an alternative approach directly applicable to in vivo applications, one of the two identical optical domes of PillCAM ESO® can be engineered to have two unidirectional filters coated on the dome. One permits white light generated from an LED to exit and excite an activated Cathepsin B probe (at 610-680 nm) previously administered to mouse subjects and localized and activated in adenomatous polyps. The other filter permits NIRF at 680-720 nm emitted by the activated probe to enter and be captured by the capsule.

A Cathepsin B-sensitive probe (at 610-680 nm) was first administered to mouse subjects, wherein it then localized in and was activated by Cathepsin B expressed in adenomatous polyps. Treated tissue was then excised and imaged as disclosed below.

In light-tight chamber 124, the PillCAM ESO® was moved mechanically in the same fashion as described in Example 2, with the optical dome end and interceding filter facing the dissected GI tract. Fluorescent images were collected and transmitted through a CMOS imager in the PILLCAM ESO® to the recorder, which was further analyzed as described in Example 2. The light sensor at the opposite end of capsule was turned off for this experiment. The sensitivity and specificity in detection of dysplastic adenoma from both an existing NIRF reflectance imaging system and the filter-modified PillCAM ESO® system was compared.

This study provides proof of principle that VCE imaging can be modified to permit testing of molecular probes that distinguish well characterized benign versus premalignant or malignant lesions in different mouse models.

As more and more NIRF and other imaging probes activated by enzymes associated with different disease processes become available, it is envisioned that the subject matter disclosed herein can be used for detection and differentiation of inflammatory diseases, such as Crohn's disease and other diseases, versus malignant infiltrative processes, such as lymphoma for example. Lesions associated with inflammatory processes (ulcerations caused for example by Crohn's disease) can also be distinguished from those induced by medications (for example, ulcerations caused by NSAIDs). This ability to differentiate drastically different disease processes is extremely advantageous and beneficial and provides an invaluable medical application and tool in further medical decision making.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. An imaging system for in vivo imaging, the imaging system comprising:
   (a) a video imaging system comprising:
      (i) a video imaging device adapted for passage within any portion of a gastrointestinal tract for imaging an area of interest from within an entire gastrointestinal tract, the video imaging device comprising an optical system for in vivo imaging adapted for detection of electromagnetic radiation, an electromagnetic radiation source, a transmitter for transmitting images from the optical system, and a power source; and
      (ii) a receiver for receiving images transmitted from the video imaging device; and
   (b) a biological probe comprising a fluorochrome with absorption and emission maximum between 600 and 1300 nm and one or more fluorochrome quencher molecules for targeting and attaching to an in vivo probe target;
   further wherein the video imaging device is swallowable and comprises an electromagnetic radiation filter for filtering electromagnetic radiation passing from and to the video imaging device, the filter comprising an excitation filter adapted to pass light between approximately 610 nm and 650 nm and an emission filter adapted to pass red and near infrared fluorescent (NIRF) light between approximately 680 nm and 720 nm; whereby the video imaging system is adapted to image the emission wavelength and visually identify diseased tissue, non-diseased tissue, or both diseased tissue and non-diseased tissue at the probe target within the transmitted images from the video imaging system.

2. The imaging system of claim 1 wherein the biological probe comprises one or more self-quenching fluorochrome molecules.

3. The imaging system of claim 1 wherein the biological probe comprises a targeting moiety adapted to target the biological probe to the probe target.

4. The imaging system of claim 3 wherein the targeting moiety is selected from the group consisting of a membrane translocation signal, an antibody, an antigen-binding antibody fragment, and a receptor-binding molecule.

5. The imaging system of claim 1 wherein the biological probe is an activatable biological probe.

6. The imaging system of claim 5 wherein the activatable probe is maintained in a non-active form by intramolecular quenching of the fluorochrome.

7. The imaging system of claim 5 wherein the activatable probe is activatable by a protease expressed by the probe target.

8. The imaging system of claim 7 wherein the protease is selected from the group consisting of a cathepsin, a caspase, and a matrix metalloproteinase.

9. The imaging system of claim 1, wherein the biological probe further comprises a protective molecule to decrease immunogenicity of the probe, increase plasma half-life, or facilitate cell internalization.

* * * * *

SEQUENCE LISTING

<160> NUMBER OF SEQ ID NOS: 16

<210> SEQ ID NO 1
<211> LENGTH: 9
<212> TYPE: PRT
<213> ORGANISM: Artificial Sequence
<220> FEATURE:
<223> OTHER INFORMATION: binding sequence for Somatostatin
<220> FEATURE:
<221> NAME/KEY: DISULFID
<222> LOCATION: (3)..(8)
<220> FEATURE:
<221> NAME/KEY: MISC_FEATURE
<222> LOCATION: (5)..(5)
<223> OTHER INFORMATION: Xaa is D-Trp

<400> SEQUENCE: 1

Asp Phe Cys Tyr Xaa Lys Thr Cys Thr
1               5

<210> SEQ ID NO 2
<211> LENGTH: 11
<212> TYPE: PRT
<213> ORGANISM: Artificial Sequence
<220> FEATURE:
<223> OTHER INFORMATION: binding sequence for Bombesin

<400> SEQUENCE: 2

Gly Ser Gly Gln Trp Ala Val Gly His Leu Met
1               5                   10

<210> SEQ ID NO 3
<211> LENGTH: 8
<212> TYPE: PRT
<213> ORGANISM: Artificial Sequence
<220> FEATURE:
<223> OTHER INFORMATION: substrate sequence for Cathepsin K

<400> SEQUENCE: 3

Gly Gly Pro Arg Gly Leu Pro Gly
1               5

<210> SEQ ID NO 4
<211> LENGTH: 9
<212> TYPE: PRT
<213> ORGANISM: Artificial Sequence
<220> FEATURE:
<223> OTHER INFORMATION: substrate sequence for Cathepsin D
<220> FEATURE:
<221> NAME/KEY: MISC_FEATURE
<222> LOCATION: (4)..(4)
<223> OTHER INFORMATION: Xaa is Cys (Et), which is ethylcysteine

<400> SEQUENCE: 4

Gly Pro Ile Xaa Phe Phe Arg Leu Gly
1               5

<210> SEQ ID NO 5
<211> LENGTH: 7
<212> TYPE: PRT
<213> ORGANISM: Artificial Sequence
<220> FEATURE:
<223> OTHER INFORMATION: substrate sequence for MMP-2

<400> SEQUENCE: 5

Gly Pro Leu Gly Val Arg Gly
1               5

-continued

```
<210> SEQ ID NO 6
<211> LENGTH: 9
<212> TYPE: PRT
<213> ORGANISM: Artificial Sequence
<220> FEATURE:
<223> OTHER INFORMATION: substrate sequence for MMP-7

<400> SEQUENCE: 6

Gly Val Pro Leu Ser Leu Thr Met Gly
1               5

<210> SEQ ID NO 7
<211> LENGTH: 8
<212> TYPE: PRT
<213> ORGANISM: Artificial Sequence
<220> FEATURE:
<223> OTHER INFORMATION: substrate sequence for MMP-7

<400> SEQUENCE: 7

Arg Pro Leu Ala Leu Trp Arg Ser
1               5

<210> SEQ ID NO 8
<211> LENGTH: 15
<212> TYPE: PRT
<213> ORGANISM: Artificial Sequence
<220> FEATURE:
<223> OTHER INFORMATION: substrate sequence for uPA

<400> SEQUENCE: 8

Gly Gly Leu Gly Gln Arg Gly Arg Ser Ala Asn Ala Ile Leu Glu
1               5                   10                  15

<210> SEQ ID NO 9
<211> LENGTH: 6
<212> TYPE: PRT
<213> ORGANISM: Artificial Sequence
<220> FEATURE:
<223> OTHER INFORMATION: substrate sequence for Caspase-1

<400> SEQUENCE: 9

Gly Trp Glu His Asp Gly
1               5

<210> SEQ ID NO 10
<211> LENGTH: 8
<212> TYPE: PRT
<213> ORGANISM: Artificial Sequence
<220> FEATURE:
<223> OTHER INFORMATION: substrate sequence for Caspase-3

<400> SEQUENCE: 10

Gly Asp Glu Val Asp Gly Ser Gly
1               5

<210> SEQ ID NO 11
<211> LENGTH: 10
<212> TYPE: PRT
<213> ORGANISM: Artificial Sequence
<220> FEATURE:
<223> OTHER INFORMATION: substrate sequence for HIV-encoded protease

<400> SEQUENCE: 11

Gly Val Ser Gln Asn Tyr Pro Ile Val Gly
1               5                   10
```

```
<210> SEQ ID NO 12
<211> LENGTH: 10
<212> TYPE: PRT
<213> ORGANISM: Artificial Sequence
<220> FEATURE:
<223> OTHER INFORMATION: substrate sequence for HSV-encoded protease

<400> SEQUENCE: 12

Leu Val Leu Ala Ser Ser Ser Phe Gly Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: substrate sequence for Cytomegalovirus-encoded
      protease

<400> SEQUENCE: 13

Gly Val Val Gln Ala Ser Cys Arg Leu Ala
1               5                   10

<210> SEQ ID NO 14
<211> LENGTH: 6
<212> TYPE: PRT
<213> ORGANISM: Artificial Sequence
<220> FEATURE:
<223> OTHER INFORMATION: substrate sequence for Thrombin
<220> FEATURE:
<221> NAME/KEY: MISC_FEATURE
<222> LOCATION: (2)..(2)
<223> OTHER INFORMATION: Xaa is D-Phe
<220> FEATURE:
<221> NAME/KEY: MISC_FEATURE
<222> LOCATION: (3)..(3)
<223> OTHER INFORMATION: Xaa is pipecolic acid

<400> SEQUENCE: 14

Gly Xaa Xaa Arg Ser Gly
1               5

<210> SEQ ID NO 15
<211> LENGTH: 6
<212> TYPE: PRT
<213> ORGANISM: Artificial Sequence
<220> FEATURE:
<223> OTHER INFORMATION: substrate sequence for Prostate-specific
      antigen

<400> SEQUENCE: 15

His Ser Ser Lys Leu Gln
1               5

<210> SEQ ID NO 16
<211> LENGTH: 6
<212> TYPE: PRT
<213> ORGANISM: Artificial Sequence
<220> FEATURE:
<223> OTHER INFORMATION: substrate sequence for Interleukin 1
      beta-converting enzyme

<400> SEQUENCE: 16

Gly Trp Glu His Asp Gly
1               5
```